(12) United States Patent
Yokota

(10) Patent No.: US 6,768,022 B2
(45) Date of Patent: Jul. 27, 2004

(54) METHOD FOR PRODUCING THIOSALICYLIC ACID

(75) Inventor: Keiichi Yokota, Kashima (JP)

(73) Assignee: Air Water Chemical Inc., Tokyo (JP)

( * ) Notice: Subject to any disclaimer, the term of this patent is extended or adjusted under 35 U.S.C. 154(b) by 0 days.

(21) Appl. No.: 10/315,985

(22) Filed: Dec. 11, 2002

(65) Prior Publication Data

US 2004/0116734 A1 Jun. 17, 2004

(51) Int. Cl.[7] .................... C07C 381/00; C07C 315/00
(52) U.S. Cl. ........................................ 562/432; 568/29
(58) Field of Search ............................ 562/432; 568/29

(56) References Cited

FOREIGN PATENT DOCUMENTS

| JP | 57-11961 A | 1/1982 |
|----|------------|--------|
| JP | 64-11017 B2 | 2/1989 |
| JP | 11-140045 A | 5/1999 |

OTHER PUBLICATIONS

Organic Syntheses and Thiosalicylic Acid, Allen et al, 1943, p. 580.

*Primary Examiner*—Ba K. Trinh
*Assistant Examiner*—Taylor V. Oh
(74) *Attorney, Agent, or Firm*—Birch, Stewart, Kolasch & Birch, LLP

(57) ABSTRACT

The present invention relates to a method for causing sodium sulfide or a mixture of sodium sulfide and sulfur to react with diazonium salt formed by diazotizing anthranilic acid, wherein the Na/S atomic ratio as calculated on the basis of the employed sodium sulfide and sulfur is adjusted to within the range of 1.33 to 2.0 during the reaction. Thus is made practicable the manufacture of thiosalicylic acid in a high yield without going through the individual route of isolating and reducing dithiosalicylic acid.

7 Claims, No Drawings

METHOD FOR PRODUCING THIOSALICYLIC ACID

FIELD OF THE INVENTION

The present invention relates to a method for efficiently producing thiosalicylic acid which is a useful intermediate in the manufacture of medicines, pesticides, dyes, etc. More particularly, the present invention relates to a process for manufacturing thiosalicylic acid from anthranilic acid in a two step reactive process.

DESCRIPTION OF THE RELATED ART

The process for manufacturing thiosalicylic acid from anthranilic acid as the raw material has been historically known. This process generally necessitates the following three-step reactive process. That is to say, firstly anthranilic acid is converted to diazonium salt by reaction with sodium nitrite in hydrochloric acid; secondly, the resulting salt is converted to dithiosalicylic acid by reaction with an equimolar mixture of sodium sulfide and sulfur; and thirdly and lastly the resulting dithiosalicylic acid is converted to thiosalicylic acid by reduction by zinc in acetic acid solvent (Org. Synth. Coll., vol. 2, p 580(1943)). This three-step reactive process is illustrated in the following diagrams.

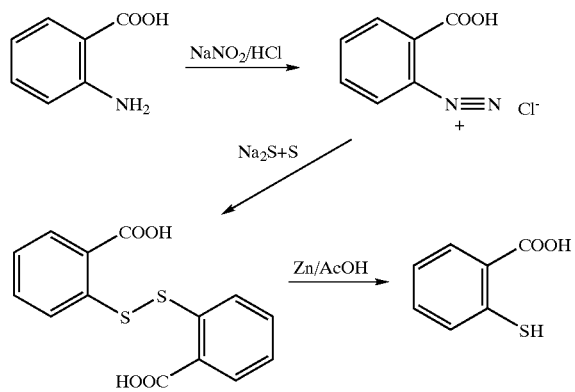

As for the third step in the above diagram which constitutes the process to reduce dithiosalicylic acid, there have been proposed some number of various processes, such as the method based on reduction by a metal selected from among zinc, aluminum, and tin in aqueous solution of an alkali metal hydroxide (Japan Laid-open Patent Application No. Hei-11 (1999)-140045), the method based on reduction by a metal like zinc, iron, etc., which generates hydrogen by reaction with acid, and a hydrogen halide in a lower aliphatic alcohol solvent (Japan Laid-open Patent Application No. Sho-57 (1982)-11961), and the method based on reduction by hydrogen in the presence of a Raney nickel catalyst in aqueous solution of an alkali (Japanese Patent No. Sho-64 (1989)-11017).

Notwithstanding their time-honored positions, those manufacturing methods can be hardly said satisfactory from the contemporary industrial standpoint, for they disclose certain problematic aspects. Above all, in those processes for synthesizing thiosalicylic acid from anthranilic acid some sort of reductive step has to be followed through after the isolation of dithiosalicylic acid. Obviously, the isolation of dithiosalicylic acid constitutes an indispensable element of the whole process. Such need to run a multi-step operation no doubt makes those processes less economical, and, moreover, the reductive step adds to disadvantages due to inevitable requirements for disposal of waste liquids, waste water, etc. In particular, so long as zinc or another metal is employed for the reduction, the waste disposal problem involving metal containing sulfur compounds remains to be resolved.

SUMMARY OF THE INVENTION

Under the circumstance, the present inventor has made keen research efforts to develop such a simpler process for producing thiosalicylic acid that would do away with the isolation of dithiosalicylic acid, thus dispensing with the reductive reaction step. In the arena of the manufacture of thiosalicylic acid based on the conversion of anthranilic acid into diazonium salt by diazotization, such reaction needs to be followed by its reaction with sodium sulfide along with sulfur. The present inventor, as the result of such efforts, discovered that thiosalicylic acid, the target product, can be directly produced in a high yield by means of adjusting the ratio between sodium sulfide and sulfur, while these chemicals have been historically utilized in production of dithiosalicylic acid (the intermediate), and what thus has been finally arrived at is the present invention.

It is, therefore, the object of the present invention to provide an economical process for manufacturing thiosalicylic acid which is able to dispense with the individual process of isolating and reducing dithiosalicylic acid.

According to the invention there is provided a manufacturing process for producing thiosalicylic acid which comprises reacting diazonium salt formed by diazotizing anthranilic acid with sodium sulfide or a mixture of sodium sulfide and sulfur under such condition that the sodium to sulfur (Na/S) atomic ratio as calculated on the basis of the employed sodium sulfide and sulfur is fixed to within the range of 1.33 to 2.0.

DETAILED DESCRIPTION

The time-honored reaction of diazotizing anthranilic acid is carried out typically by reacting it with a mineral acid and sodium nitrite in aqueous solution. Although choice of the mode of reaction is optional, it is the typical practice to add sodium nitrite or an aqueous solution of sodium nitrite to aqueous solution of a mineral acid into which anthranilic acid has been dissolved beforehand.

There can be cited hydrochloric acid and sulfuric acid as a few examples of the mineral acid to be employed for the diazotization reaction. The amount of mineral acid to be employed per mole of anthranilic acid is to be preferably in the range of 1.3 to 10.0 moles, and more preferably 1.5 to 5.0 moles. In cases where the amount of mineral acid is too short, the yield of diazonium salt drops off, and where it is on the contrary excessively large, the efficiency declines, even though the reaction per se is not adversely affected. Therefore, neither case is desirable.

As for the type of water to be selected for use in the reaction as disclosed in the present invention, industrial water, ion-exchanged water, pure water, and distilled water are all suitably useable. The amount of water to be employed in the diazotizing reaction is to be preferably 1.5 to 10.0 times, and particularly preferably 2.0 to 5.0 times as much as anthranilic acid by weight. In cases where the amount of water is too short, the concentration of the crystal of the mineral acid salt formed from anthranilic acid in the reactant liquid gets too high to employ agitation. In cases where the amount of water is excessively large, the yield drops off, even though the reaction is not disrupted at all. Hence, neither case is desirable.

For diazotization of anthranilic acid, sodium nitrite is employed as the diazotizing agent. Sodium nitrite which is available normally in the solid state may be added to the reaction system as it is, while the typical practice is to employ it in the state of being dissolved in water. The amount of sodium nitrite per mole of the raw material anthranilic acid is to be preferably in the range of 0.8 to 1.5 moles, and more preferably in the range of 0.9 to 1.4 moles. In cases where the amount of sodium nitrite is too short, the conversion rate of the raw material declines to an undesirable degree. On the contrary, impurities in the reaction product increase with use of an excessive amount of sodium nitrite. Therefore, neither case is desirable. As for the fashion of adding sodium nitrite, there is imposed no particular limitation. That is to say, it may be added by dropping or pouring into the reactant liquid.

The temperature at which addition and reaction of sodium nitrite are to be made may be set within the range of 10° C. below zero to 30° C., and preferably zero to 20° C. With reaction temperatures kept to below the lower ends of said ranges, the reaction rate gets slower. On the contrary, when the reaction temperature exceeds the upper end of said ranges, decomposition of diazonium salt progresses with the result that the yield drops off and more impurities come to be included. Therefore, deviation from said ranges is by no means desirable.

There is no particular limitation to the time frame in which addition of sodium nitrite is to be completed, but the time frame may be regulated in the light of the state of bubbling of generated nitrogen gas and cooling capacity. It is typically 0.1 to 24 hr. The reaction may be terminated as soon as the addition of sodium nitrite is finished, although the reaction is to be terminated typically after having stirred the reactants for 0.1 to 3 hr.

As for the reaction caused to take place according to the present invention between the diazonium salt thus formed from anthranilic acid and sodium sulfide or a mixture of sodium sulfide and sulfur, the sodium to sulfur (Na/S) atomic ratio as calculated on the basis of the employed sodium sulfide and sulfur is to be adjusted to 1.33 to 2.0. That is to say, sodium monosulfide, known as $Na_2S$, may be used singularly. Otherwise, there may be employed a mixture of sodium monosulfide and sodium polysulfide, the latter being known as $Na_2S_x$ (x=2–5), whose (the mixture's) sodium to sulfur (Na/S) atomic ratio is to be in the range of 1.33 to 2.0 or a mixture of sodium monosulfide and sulfur (a mixture of $Na_2S$/S admixed by the molar ratio of 1/0 to 2/1), whose (the mixture's) sodium to sulfur (Na/S) atomic ratio is to be in the range of 1.33 to 2.0, or the like. From the industrial standpoint, it is preferable that sodium monosulfide be employed singularly or in combination with sulfur as a mixture of the two chemicals. While it is inferred that in the course of these reactive processes dithiosalicylic acid is produced temporarily and subsequently converted to thiosalicylic acid by reduction, it is not a desirable situation that the ratio of sulfur contained in those thiolizing agents exceed the aforesaid ranges because an excessive sulfur content gives rise to retarded reduction of dithiosalicylic acid, a decline in the yield of thiosalicylic acid, and increased production of dithiosalicylic acid compared with the amount of thiosalicylic acid produced.

The aforesaid reaction is suitably carried out by bringing the liquid prepared by adding sodium sulfide or sodium sulfide along with sulfur to water into contact with the aqueous solution of diazonium salt formed from anthranilic acid. Any amount of water may be employed for the former liquid so long as it is enough in quantity to permit stirring of sodium sulfide or sodium sulfide along with sulfur. Typically, water is employed by a ratio of 0.5 to 10.0 times as much as sodium sulfide by weight. There is also added alkali such as sodium hydroxide, potassium hydroxide, etc. in an amount of about 0.5 to 3 equivalents against the mineral acid employed for diazotization so as to keep the reaction system alkaline. The preferred method for carrying out the aforesaid reaction is to drop the aqueous solution of diazonium salt formed from anthranilic acid into the liquid prepared by adding sodium sulfide or sodium sulfide along with sulfur to water. As the aqueous solution of such a diazonium salt, there may be employed the reaction mixture obtained by the diazotization reaction as it is.

The amount of sodium sulfide or sodium sulfide along with sulfur to be employed in said reaction is to be preferably 0.9 to 5.0 moles, and more preferably 0.95 to 2.0 moles on the basis of sulfur atom per mole of diazonium salt formed from anthranilic acid. The grounds for selecting said ratios are that in cases where the amount of sodium sulfide or sodium sulfide along with sulfur is too little, the achievable yield of thiosalicylic acid is only so low and that if the amount is excessive, the resultant effects are a low purity, increased impurities and a decline in the production efficiency for thiosalicylic acid.

It is desirable that the temperature at which the aqueous solution of diazonium salt formed from anthranilic acid is added and reacted is fixed within the range of 10° C. below zero to 100° C., and particularly zero to 80° C. At temperatures lower than the aforesaid temperatures the rate of reaction gets too low, and, on the other hand, at higher temperatures the yield drops off.

There is no particular limitation to the time frame in which addition of the aqueous solution of diazonium salt formed from anthranilic acid is to be completed. The time frame may be regulated in accordance with cooling capacity. It is typically 0.1 to 24 hr. From the point in time where the aqueous solution finishes to be added, however, it is preferable to terminate the reaction after having stirred the reactant for further 0.1 to 10 hr.

Thiosalicylic acid can be retrieved in the crystalline form by acidifying the mixture of reaction products thus obtained with a mineral acid. There can be cited hydrochloric acid and sulfuric acid as a few examples of such mineral acid. The amount of mineral acid to be employed may correspond to such level where the system gets acidic enough to let thiosalicylic acid precipitate in the crystalline form, e.g. a pH of 3 or less. As for the concentration of mineral acid employed in this case, 35% concentrated hydrochloric acid or a diluted hydrochloric acid prepared by diluting it with water or sulfuric acid of a comparable concentration may be used. For the process of precipitating with acid, it is preferable to adopt the method of adding said thiolized reaction mixture to the aqueous solution of mineral acid. In case the addition is made in the opposite order, the oxidative reaction of thiosalicylic acid is apt to progress and consequently the dithiosalicylic acid content of the obtained thiosalicylic acid tends to be augmented.

Precipitated crystals can be retrieved by a conventional technique of separation, such as centrifugal separation, filtration under reduced pressure, etc. In cases where products are required to have high purity, the thiosalicylic acid thus obtained may be referred to a purification step in which it is purified by re-crystallization using an organic solvent such as alcohol and ethyl acetate.

The present invention is illustrated in more details in reference with the following examples, in which "%" as used for the concentration denotes "% by weight" and "%" for the yield "mole %."

EXAMPLE 1

13.7 g (0.1 mole) of anthranilic acid, 41.1 g of water, and 20.86 g (0.2 mole) of 35% hydrochloric acid were charged into a 100-ml glass flask equipped with agitator and thermometer. The charged materials were cooled to a temperature of 5° C. while agitation was employed. Next, an aqueous solution prepared by dissolving 7.25 g (0.105 mole) of sodium nitrite in 13.5 g of water was dropped into the thus obtained reactant liquid using a dropping funnel over 30 min. with the temperature maintained at 5° C. or below and the same temperature level was maintained for another 30 min.

Charged into a 200-ml glass flask equipped with agitator, thermometer, and reflux condenser, separate from the aforesaid glass flask, were 21.6 g (0.09 mole) of sodium sulfide 9 hydrate, 0.64 g (0.02 mole) of sulfur, 24 g of water, and 12.5 g (0.15 mole) of 48% aqueous solution of sodium hydroxide, which were thereupon cooled to a temperature of 5° C. while agitation was employed throughout. Next, the aforesaid diazotized aqueous solution was dropped into the thus obtained reactant liquid using a dropping funnel over 1 hr with the temperature maintained at 5° C. or below and the reaction was allowed to progress for further 1 hr at room temperature and for further 2 hr at a temperature of 60° C., respectively, whereupon the reaction was terminated.

Upon termination of the reaction the reaction mixture was cooled down and added to 84 g of 10% hydrochloric acid for crystallizing thiosalicylic acid. The precipitated crystalline matters were filtered out and dried into 15.5 g of crystalline matters. Liquid chromatography analysis of the obtained crystalline matters revealed that the components comprised 83.2% of thiosalicylic acid and 2.6% of dithiosalicylic acid. The yield of thiosalicylic acid was 83.7%. Pertinent test results are summarized in Table 1.

EXAMPLES 2–6

Shown in Table 1 are results of a test conducted by following the same procedure as in Example 1 except that the ratio of sodium sulfide to sulfur and the amount of sodium sulfide were changed to those which are indicated in Table 1, respectively.

TABLE 1

|  | Examples | | | | | |
|---|---|---|---|---|---|---|
|  | 1 | 2 | 3 | 4 | 5 | 6 |
| Diazotization |  |  |  |  |  |  |
| Anthranilic acid (mole) | 0.10 | 0.10 | 0.10 | 0.10 | 0.10 | 0.10 |
| Water (g) | 41.1 | 34.3 | 34.3 | 36.7 | 34.3 | 34.3 |
| 35% hydrochloric acid (mole) | 0.20 | 0.20 | 0.20 | 0.20 | 0.20 | 0.20 |
| Sodium nitrite (mole) | 0.105 | 0.098 | 0.105 | 0.105 | 0.105 | 0.105 |
| Thiolization |  |  |  |  |  |  |
| Sodium sulfide (mole) | 0.09 | 0.08 | 0.11 | 0.10 | 0.095 | 0.12 |
| Sulfur (mole) | 0.02 | 0.02 |  |  |  |  |
| Na/S (atomic ratio) | 1.64 | 1.60 | 2.0 | 2.0 | 2.0 | 2.0 |
| Sodium hydroxide (mole) | 0.15 | 0.20 | 0.11 | 0.11 | 0.11 | 0.11 |
| Water (g) | 24.0 | 12.0 | 26.4 | 24.0 | 22.8 | 24.0 |
| Diazotized mixture dropping temperature (° C.) | <5 | <5 | <5 | <5 | <5 | <5 |
| Thiosalicylic acid |  |  |  |  |  |  |
| Yield by quantity (g) | 15.5 | 14.3 | 14.6 | 14.4 | 13.9 | 14.8 |
| Purity |  |  |  |  |  |  |
| Thiosalicylic acid (wt %) | 83.2 | 74.3 | 83.0 | 82.7 | 77.5 | 70.9 |
| Dithiosalicylic acid (wt %) | 2.6 | 0.3 | 1.4 | 2.7 | 11.6 | 1.4 |
| Yield (mole %) | 83.7 | 69.2 | 78.7 | 77.5 | 70.0 | 68.4 |

EXAMPLES 7–12

Shown in Table 2 are results of a test conducted by following the same procedure as in Example 1 except that the amount of hydrochloric acid, the diazotized reaction mixture dropping temperature, the amount of sodium nitrite and the kind of mineral acid were changed to those which are indicated in Table 2, respectively.

TABLE 2

|  | Examples | | | | | |
| --- | --- | --- | --- | --- | --- | --- |
|  | 7 | 8 | 9 | 10 | 11 | 12 |
| Diazotization |  |  |  |  |  |  |
| Anthranilic acid (mole) | 0.10 | 0.10 | 0.10 | 0.10 | 0.10 | 0.10 |
| Water (g) | 41.1 | 41.1 | 41.1 | 41.1 | 34.3 | 41.1 |
| 35% hydrochloric acid (mole) | 0.15 | 0.20 | 0.20 | 0.20 | 0.20 | 0.15* |
| Sodium nitrite (mole) | 0.105 | 0.105 | 0.105 | 0.09 | 0.095 | 0.098 |
| Thiolization |  |  |  |  |  |  |
| Sodium sulfide (mole) | 0.09 | 0.09 | 0.09 | 0.09 | 0.09 | 0.09 |
| Sulfur (mole) | 0.02 | 0.02 | 0.02 | 0.02 | 0.02 | 0.02 |
| Na/S (atomic ratio) | 1.64 | 1.64 | 1.64 | 1.64 | 1.64 | 1.64 |
| Sodium hydroxide (mole) | 0.15 | 0.15 | 0.15 | 0.15 | 0.10 | 0.20 |
| Water (g) | 24.0 | 24.0 | 24.0 | 24.0 | 13.7 | 12.0 |
| Diazotized mixture dropping temperature (° C.) | <5 | 20–30 | 55–60 | 20–30 | 20–30 | 20–30 |
| Thiosalicylic acid |  |  |  |  |  |  |
| Yield by quantity (g) | 15.5 | 14.2 | 14.0 | 12.9 | 14.0 | 14.1 |
| Purity |  |  |  |  |  |  |
| Thiosalicylic acid (wt %) | 80.4 | 83.2 | 75.7 | 79.6 | 73.4 | 76.2 |
| Dithiosalicylic acid (wt %) | 2.9 | 3.3 | 2.5 | 0.9 | 0.8 | 1.1 |
| Yield (mole %) | 81.1 | 76.6 | 68.6 | 66.8 | 66.9 | 69.7 |

*sulfuric acid was used in place of hydrochloric acid

COMPARATIVE EXAMPLES 1–3

Shown in Table 3 are results of a test conducted by following the same procedure as in Example 1 except that the ratio of sodium sulfide to sulfur, the amount of sodium sulfide and sulfur and the method of precipitation with acid were changed, respectively.

TABLE 3

|  | Comparative Examples | | |
| --- | --- | --- | --- |
|  | 1 | 2 | 3* |
| Diazotization |  |  |  |
| Anthranilic acid (mole) | 0.10 | 0.10 | 0.10 |
| Water (g) | 41.1 | 41.1 | 41.1 |
| 35% hydrochloric acid (mole) | 0.20 | 0.20 | 0.20 |
| Sodium nitrite (mole) | 0.105 | 0.105 | 0.105 |
| Thiolization |  |  |  |
| Sodium sulfide (mole) | 0.05 | 0.07 | 0.11 |
| Sulfur (mole) | 0.06 | 0.04 | 0.11 |
| Na/S (atomic ratio) | 0.91 | 1.27 | 1.0 |
| Sodium hydroxide (mole) | 0.30 | 0.30 | 0.10 |
| Water (g) | 24.0 | 24.0 | 29.0 |
| Diazotized mixture dropping temperature (° C.) | <5 | <5 | <5 |
| Thiosalicylic acid |  |  |  |
| Yield by quantity (g) | 15.6 | 15.7 | 7.5 |
| Purity |  |  |  |
| Thiosalicylic acid (wt %) | 34.5 | 58.0 | 46.7 |
| Dithiosalicylic acid (wt %) | 55.1 | 31.9 | 23.9 |
| Yield (mole %) | 34.9 | 59.1 | 22.6 |

*: The precipitation with acid was carried out by adding 35% hydrochloric acid into the thiolized reaction mixture.

Up to date the manufacture of thiosalicylic acid from anthranilic acid has necessitated the 3-step reactive process. The present invention renders it possible to manufacture the same target product from the same starting raw material in two reactive steps, instead. What can be accomplished by the process disclosed in the present invention are greater economy achieved with the less number of manufacturing steps and mitigated operational and ecological burdens of industrial-waste disposal.

What I claim is:

1. A method for producing thiosalicylic acid which comprises reacting sodium sulfide or a mixture of sodium sulfide and sulfur with a diazonium salt to produce thiosalicylic acid, wherein the sodium to sulfur (Na/S) atomic ratio as calculated on the basis of the employed sodium sulfide and sulfur is within the range of 1.33 to 2.0, wherein said diazonium salt is formed by diazotizing anthranilic acid.

2. The method for producing thiosalicylic acid as described in claim 1, wherein the amount of sodium sulfide or a mixture of sodium sulfide and sulfur to be employed per mole of said diazonium salt is adjusted to 0.9 to 5.0 moles as calculated on the basis of sulfur atom.

3. The method for producing thiosalicylic acid as described in claim 2, wherein the reaction of said diazonium salt with sodium sulfide or a mixture of sodium sulfide and sulfur is carried out under such condition that alkali is added throughout.

4. The method for producing thiosalicylic acid as described in claim 3, wherein the mixture of reaction products formed by the reaction of said diazonium salt with sodium sulfide or a mixture of sodium sulfide and sulfur is added to an aqueous solution of mineral acid to precipitate thiosalicylic acid.

5. The method for producing thiosalicylic acid as described in claim 1, wherein the reaction of said diazonium salt with sodium sulfide or a mixture of sodium sulfide and sulfur is carried out under such condition that alkali is added throughout.

6. The method for producing thiosalicylic acid as described in claim 5, wherein the mixture of reaction products formed by the reaction of said diazonium salt with sodium sulfide or a mixture of sodium sulfide and sulfur is added to an aqueous solution of mineral acid to precipitate thiosalicylic acid.

7. The method for producing thiosalicylic acid as described in claim 1, wherein the mixture of reaction products formed by the reaction of said diazonium salt with sodium sulfide or a mixture of sodium sulfide and sulfur is added to an aqueous solution of mineral acid to precipitate thiosalicylic acid.

* * * * *